US007734390B2

(12) United States Patent
Chen

(10) Patent No.: US 7,734,390 B2
(45) Date of Patent: Jun. 8, 2010

(54) USE OF AUTOMOTIVE DIAGNOSTICS CONSOLE TO DIAGNOSE VEHICLE

(75) Inventor: Ieon C. Chen, Laguna Hills, CA (US)

(73) Assignee: Innova Electronics, Corp, Fountain Valley, CA (US)

( * ) Notice: Subject to any disclaimer, the term of this patent is extended or adjusted under 35 U.S.C. 154(b) by 744 days.

(21) Appl. No.: 11/657,332

(22) Filed: Jan. 24, 2007

(65) Prior Publication Data

US 2007/0124040 A1    May 31, 2007

Related U.S. Application Data

(63) Continuation-in-part of application No. 09/961,223, filed on Sep. 21, 2001, now Pat. No. 6,941,203.

(51) Int. Cl.
G01M 17/00    (2006.01)
G06F 19/00    (2006.01)
(52) U.S. Cl. .............................. 701/33; 701/29; 701/2; 705/26
(58) Field of Classification Search ............. 701/29–35, 701/2; 705/26
See application file for complete search history.

(56) References Cited

U.S. PATENT DOCUMENTS 4,404,639 A * 9/1983 McGuire et al. ............. 701/35
5,506,772 A * 4/1996 Kubozono et al. ........... 701/29
5,758,300 A * 5/1998 Abe ........................... 455/424
5,916,286 A * 6/1999 Seashore et al. ............. 701/29
6,006,146 A * 12/1999 Usui et al. .................... 701/29
6,021,366 A * 2/2000 Fieramosca et al. .......... 701/33
6,295,492 B1 * 9/2001 Lang et al. .................... 701/33
6,434,455 B1 * 8/2002 Snow et al. ................... 701/33
2002/0156692 A1 * 10/2002 Squeglia et al. .............. 705/26

* cited by examiner

*Primary Examiner*—Tan Q Nguyen
(74) *Attorney, Agent, or Firm*—Stetina Brunda Garred & Brucker

(57) ABSTRACT

A customer driven process of diagnosing and repairing a vehicle. The process involves temporarily providing a customer with a diagnostic tool that can receive vehicle diagnostic signals from a vehicle on-board computer. The customer then uses the tool to upload diagnostic signals from the car, and returns the tool to the automotive parts/service facility. The vehicle diagnostic signals are communicated to a console, which then accesses a database(s). The database(s) includes information relating to the vehicle malfunction, the repairs needed, and the parts required to complete those repairs. The process also allows automatic scheduling of repairs and purchasing of parts from the automotive parts/service facility. Upon payment of any prescribed fees, the process outputs report information to the customer.

26 Claims, 2 Drawing Sheets

USE OF AUTOMOTIVE DIAGNOSTICS CONSOLE TO DIAGNOSE VEHICLE

CROSS-REFERENCE TO RELATED APPLICATIONS

This application is a continuation-in-part of application Ser. No. 09/961,223, filed Sep. 21, 2001 now U.S. Pat. No. 6,941,203, which is herein incorporated in its entirety by reference.

STATEMENT RE: FEDERALLY SPONSORED RESEARCH/DEVELOPMENT (Not Applicable)

BACKGROUND OF THE INVENTION

The present invention relates generally to processes used to diagnose and repair a vehicle, and more particularly to a process of quickly diagnosing a vehicle and obtaining information to ultimately repair the vehicle based on the diagnosis.

It is widely understood that vehicle care and repair can be costly. In order to mitigate the cost of vehicle care and repair, drivers often choose to fix their vehicle by themselves, performing as much maintenance as possible. However, more serious vehicle problems often must be fixed by a professional mechanic, leaving the vehicle owner to the mercy of the mechanic's repair schedule. Also, the vehicle owner is further inconvenienced because they are left without a vehicle during the repair. Thus, it is understood that there is a need to mitigate the cost and inconvenience involved in vehicle care and repair.

In addition, operation of an automotive care facility providing automotive parts and/or services (parts/services facility) can be challenging. For instance, customers desire to have their repairs completed as soon as possible; however, limited labor resources and repair space cause repair schedules to be tight. Also, since these facilities are in a competitive market, significant advertising is generated to ensure the success of the facility, but some types of advertising can be deceptively ineffective. Finally, instead of working at what they do best—repairing vehicles—mechanics often are required to spend time record keeping and helping customers with simple transactions, and since repair labor costs are not realized during this time, significant economic losses can result. Thus, it is understood that there is an ongoing need for a more effective method of operating an automotive repair facility.

One avenue of decreasing these costs and inefficiencies for both the driver and mechanic involves the computerized systems currently included on most newer vehicles. A vehicle's computer control system consists of the on-board computer and several related electronic control devices (e.g., sensors, switches, actuators, etc.). The control devices may control various systems and/or subsystems within the vehicle. These electronic control devices send information to the on-board computer related to such parameters as the temperature and density of the outside air, the speed of the engine, the amount of fuel delivered, etc. At the same time, the on-board computer scans for any problems from its sensors. If a problem is detected, the on-board computer stores the problem as a numeric code, referred to as a vehicle trouble signal or fault code, in its memory for later retrieval. In this regard, vehicle trouble signals are codes that identify a particular problem area and are intended as a guide to the proper corrective servicing of the vehicle.

Hand-held or portable code readers or scan tools, also referred to as diagnostic tools, have been utilized to troubleshoot faults or problems associated with these electronic control units. Such code readers are configured to electronically communicate with the vehicle's on-board computer for accessing stored vehicle trouble signals. When the diagnostic tool receives trouble signals from the on-board computer the trouble signals can be translated to thereby discern the vehicle malfunction.

Thus, with a hand-held diagnostic tool, a vehicle owner can diagnose their vehicle and hopefully effectuate repairs on their own. Such self-reliance can help mitigate the cost and inconvenience of vehicle repair for the vehicle owner. Also, allowing the customer to complete the minor repair tasks leaves the professional mechanic free to complete more involved (and more lucrative) tasks.

Although the use of hand-held diagnostic tools can help both the vehicle owner and the professional mechanic, the tools have not been used to do more than complete the vehicle diagnosis. Thus, it is understood that there is an ongoing need for an process by which these tools are more effectively used. Such a process would reduce the cost and inconvenience of vehicle repair for the vehicle owner, and operation of an automotive care facility would become more efficient.

BRIEF SUMMARY OF THE INVENTION

In response to the above noted needs there is disclosed a process of diagnosing a repairing a vehicle. The process may begin by receiving customer information. Such information could include credit card information, addresses and phone numbers in one embodiment. A diagnostic tool is then obtained from an automotive care business, along with instructions as to how to connect the diagnostic tool to an on-board computer of a vehicle. The diagnostic tool is connected to the on-board computer. Vehicle signals are then uploaded from the vehicle to the diagnostic tool and the diagnostic tool stores the vehicle signals. The process continues by connecting the diagnostic tool to a console and uploading the vehicle signals from the diagnostic tool to the console. A database, either local or remote, is accessed via the console and the vehicle signals are correlated with vehicle defect information in the database. The vehicle defect information is data relating to possible vehicle conditions. A vehicle defect report based on the correlation between the vehicle signals and the vehicle defect information is generated. The vehicle defect report may also be correlated with service information in the database. A service report based on the correlation between the vehicle defect report may then be generated. The service report may also be correlated with parts information in the database. Then, the vehicle defect report, the parts report, and the service report are downloaded to the console. An approval may be obtained from a customer via the console, and payment is accepted based on the approval. Finally, the vehicle defect reports, the parts reports, and/or the service reports are output.

In one embodiment, the parts report includes information relating to parts needed to complete a vehicle repair, pricing of parts, availability of parts, the location for obtaining parts, and discounts for purchasing parts. Also, in one embodiment, the service report includes information relating to needed services for completing a repair, location for obtaining services, the availability of services, the scheduling of services, the pricing for services, detailed information about the service procedure, time estimates for services, and discounts on services.

As such, this process and apparatus provide a less costly and more convenient way to complete vehicle repair because it allows a customer to obtain cheaper parts from more convenient locations, and it allows for more convenient repair scheduling. Also, automotive care businesses can be run more efficiently when this process is used because inventory and scheduling records can be updated automatically and because customers can complete transactions independently, with less need for worker intervention.

BRIEF DESCRIPTION OF THE DRAWINGS

These, as well as other features of the present invention, will become more apparent upon reference to the drawings wherein.

DETAILED DESCRIPTION OF THE INVENTION

Figure 1:
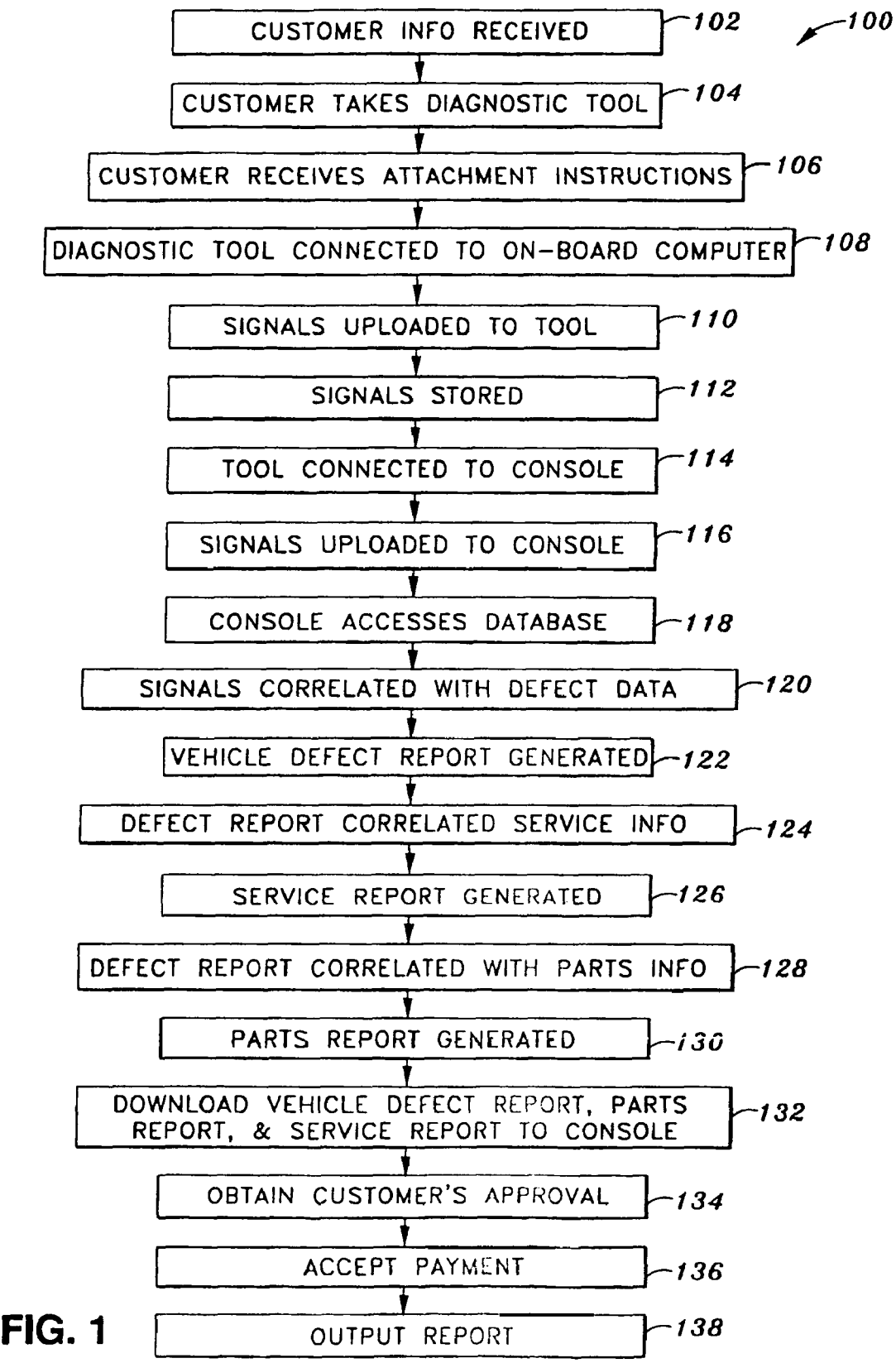
FIG. 1 is a block diagram of a process of using a hand-held diagnostic tool and a console to diagnose and obtain automotive care information.
Figure 2:
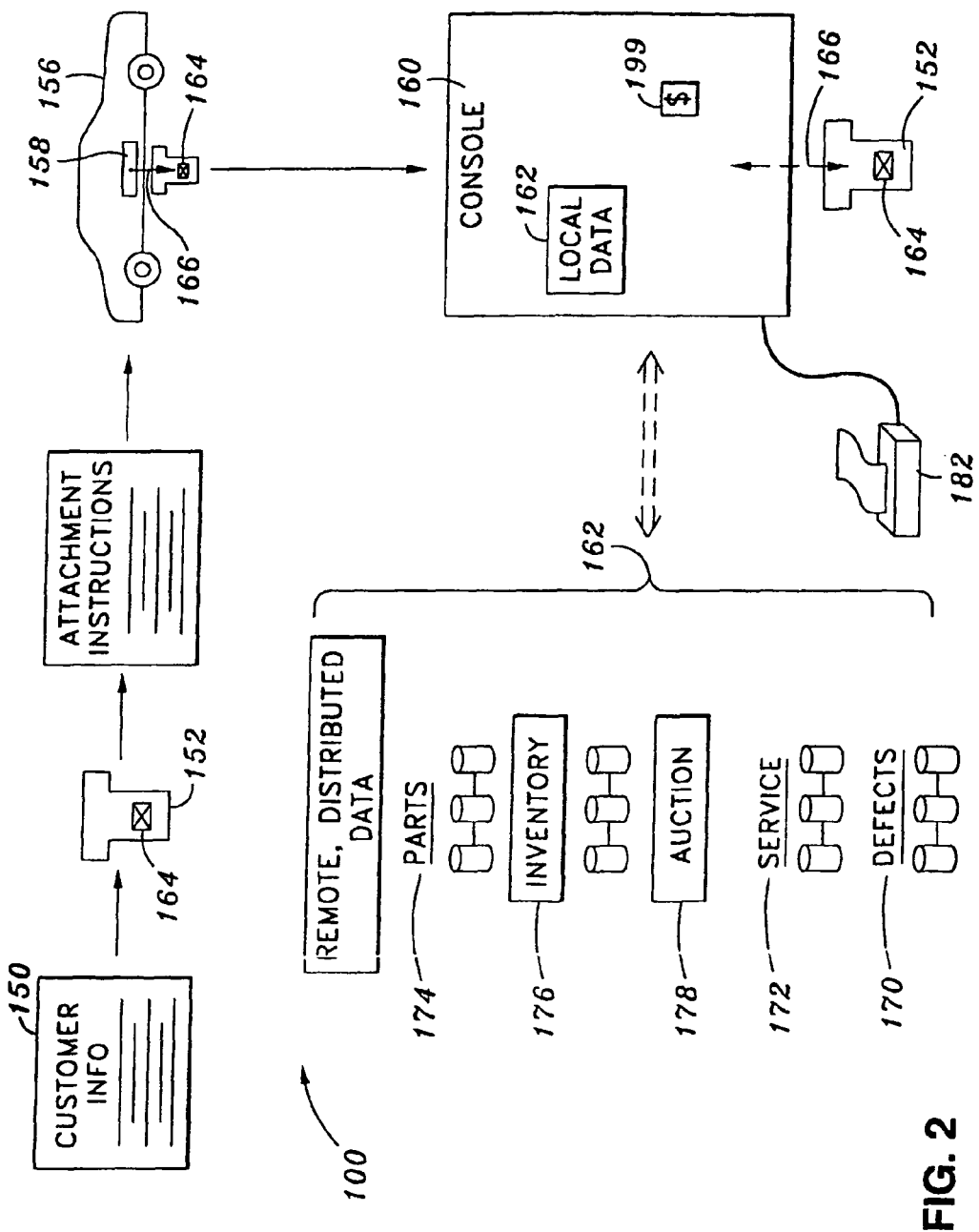
FIG. 2 is a symbolic relational diagram of the process depicted in FIG. 1.

Referring now to the drawings wherein the showings are for purposes of illustrating a preferred embodiment of the present invention only, and not for purposes of limiting the same, FIGS. 1 and 2 illustrate a process 100 by which a vehicle owner can diagnose vehicle malfunctions and obtain repair information regarding the malfunction. As shown, the process 100 involves four major elements: a diagnostic tool 152, a vehicle 156 with an on-board computer 158, a console 160, and a database 162. As will be discussed in greater detail below, when the vehicle 156 has a malfunction (e.g., sparkplug misfiring, low fluid level, etc.), the on-board computer 158 outputs pre-programmed vehicle trouble signals 166, which uniquely correspond to that particular malfunction. Also, the diagnostic tool 152 is able to receive and store those trouble signals from the on-board computer 158. The console 160 is able to communicate with the diagnostic tool 152 to receive the vehicle trouble signals 166, and the console 160 is also able to communicate with the database 162, which contains various information related to repairing the vehicle malfunction. For instance, the database 162 contains information relating to various vehicle malfunctions, repair services, and automotive parts in one embodiment.

In general, the process 100 involves connecting the diagnostic tool 152 to the on-board computer 158 of the vehicle 156 in order to transfer the vehicle trouble signals 166 to the diagnostic tool 152. Then, the diagnostic tool 152 is connected to the console 160 in order to transfer the trouble signals to the console 160. After this transfer, the console 160 communicates with the database 162 to obtain information relating to the vehicle malfunction, repair services, and parts needed to complete the repair. The console 160 also allows the information from the database 162 to be outputted to the customer for their approval. It is envisioned that such a process could be employed by an automotive care business (e.g., an automotive parts store, an automotive repair center, etc.) to decrease costs and inefficiencies for both the customer and the business. However, this process could be implemented by any other similar party skilled in the art without departing from the spirit of the invention.

Beginning at a first step 102 (FIG. 1), after a customer enters the automotive care business, the customer divulges information 150 (FIG. 2). The information 150 can include a credit card number, an address, a phone number, and information about the customer's vehicle. This information 150 is orally communicated in one embodiment, and in another embodiment, the information 150 is manually inputted into a computer, either by the customer or a worker at the automotive care business. As will be discussed in greater detail below, this information will be used later in the process to facilitate repair of the customer's vehicle.

Moving to a second step 104, the customer obtains a diagnostic tool 152. It is envisioned that the diagnostic tool 152 is owned by the automotive care business, and the tool 152 is temporarily loaned to the customer. In one embodiment, the customer pays a rental fee in order to obtain the tool 152. This rental fee can be transferred using the information received in the initial step 102 of the process 100. In another embodiment, the customer puts a deposit of money down in order to temporarily obtain the diagnostic tool 152.

Preferably, the diagnostic tool 152 is a portable device that is able to communicate with an on-board computer 158 of a vehicle 156 and receive vehicle signals therefrom. As stated above, these signals are pre-programmed to correspond to vehicle malfunctions (e.g., spark plug misfiring, etc.). Also, the diagnostic tool 152 includes a memory bank 164 such that any trouble signals received by the diagnostic tool 152 can be stored for later use.

Moving then to a third step 106 of the process 100, the customer receives attachment instructions 154, which reveal how to connect the diagnostic tool 152 to the on-board computer 158. It is envisioned that the connection method will vary depending on the type of vehicle 156 that the customer owns. In one embodiment, the attachment instructions are orally communicated to the customer by a worker at the automotive care business. In another embodiment, attachment instructions for virtually all vehicle-types are in printed form for the customer's use. In still another embodiment (not shown), the customer approaches the console 160 and the console 160 displays the attachment instructions 154 based on the customer's vehicle information obtained in the first step 102.

Once the customer has obtained attachment instructions 154, the diagnostic tool 152 is connected to the on-board computer 158 in step 108. In one embodiment, the diagnostic tool 152 electrically connects to the on-board computer 158 using a wire; however, in another embodiment, the diagnostic tool 152 wirelessly connects to the on-board computer 158.

Subsequently, in step 110, vehicle trouble signals 166 are uploaded from the on-board computer 158 to the diagnostic tool 152. Next, in step 112, the vehicle trouble signals 166 are stored in the memory bank 164 of the diagnostic tool 152.

As shown, the next step 114 commences by attaching the diagnostic tool 152 to the console 160. In one embodiment, the console 160 is owned by and located in the automotive care business. As such, the console 160 is more likely to have access to a more expansive database 162, and the customer does not have to incur the cost of purchasing the console 160.

The diagnostic tool 152 can be connected to the console 160 via a wire, or the diagnostic tool 152 can be wirelessly connected to the console 160. Once connected, step 116 commences in which the vehicle trouble signals 166 are uploaded from the diagnostic tool 152 to the console 160.

Then, in step 118, the console 160 communicates with the database 162. The database 162 contains various vehicle information, such as types of vehicle malfunctions, repair services, automotive part information, and the like, as will be discussed in greater detail below. As shown in FIG. 2, the database 162 can be local to the console 160, can be remote from the console 160, or can be a combination of a local and remote database 162.

The console 160 communicates with the remote database 162 via a computer network embodied in what is currently understood as the Internet, and the database 162 is embodied as a website with a particular web address. However, any other computer communication and/or network arrangements may also be utilized, such as local area networks (LANs), intranets, extranets, wide area networks (WANs), private networks, virtual private networks, dedicated circuits, integrated services digital networks (ISDNs), frame relay, etc. Communication between the console 160 and the remote database 162 occurs in a manner which is well known to one of ordinary skill in the art including, but not limited to, via telephone lines, cable lines (e.g., Digital Subscriber Lines (DSL) and variations thereof, wire, optical, etc.), optical communications (e.g., infrared communications), and wireless forms of communications (e.g., cellular, satellite, radio frequency (RF) transmission, and other forms of electromagnetic wave based mediums).

Preferably, the database 162 includes a wide variety of information including defect records 170, service records 172, parts records 174, inventory records 176, and an auction 178, each of which will be described in greater detail below. Such information may be contained locally to the console 160, or more preferably, the information is contained in a plurality of locations, such as parts shop web sites, repair shop web sites, automotive manufacturer web sites, and the like. Thus, in order to complete step 118, the console 160 communicates with this information.

As stated, the database 162 shown in FIG. 2, includes the defect record 170. In one embodiment, the defect record 170 includes a look-up table of various possible diagnostic trouble codes and the associated problem descriptions for each such diagnostic trouble code. As such, step 120 of the process 100 involves correlating the vehicle trouble signals 166 with the appropriate problem description in the defect information 170. In one specific embodiment of step 120, the console 160 "looks up" the vehicle trouble code 166 received from the on-board computer 158 to find a description of what that particular signal 166 means.

Once the vehicle trouble signal 166 has been correlated with the appropriate problem description, step 122 of the process 100 commences, and a vehicle defect report is generated. In one embodiment, the vehicle defect report is a saved translation of the vehicle trouble code 166, which explains what is actually wrong with the vehicle 156.

Furthermore, as is shown in FIG. 2, the database 162 includes a service record 172. The service record 172 is a compilation of information relating to types of automotive repair procedures. In one embodiment, the service record 172 includes a look-up table listing repair procedures that will fix certain vehicle malfunctions, and detailed descriptions about the repair procedures. In another more expansive embodiment, the service record 172 further includes a communications link to several automotive repair centers, and the service record 172 includes information about the types of repairs performed at each repair center, their respective locations, repair schedules, and price guides, advertising materials, and discount coupons, if available.

As such, the process 100 continues in step 124, in which the vehicle defect report (i.e., the description of the vehicle 156 malfunction) is correlated with the service record 172. In other words, step 124 associates the particular malfunction with appropriate repairs that will fix the malfunction. Also, with the expansive embodiment of the service record 172 described above, step 124 reveals how to complete the repair, where such repairs can be professionally completed, the price for such repairs, the repair schedule, and any discounts on obtaining such services.

Next, in step 126 of the process 100, a service report is generated. In one embodiment, the service report is a saved compilation of the bulk of information revealed during step 124. As will be described in greater detail below, the service report allows a customer to conveniently realize repair options, save money, and the like.

In the embodiment shown in FIG. 2, the database 162 includes a parts record 174. The parts record 174 is a compilation of information relating to automotive parts. In one embodiment, the parts record 174 includes a look-up table of parts needed to complete certain repairs and detailed descriptions about the automotive parts. In another more expansive embodiment, the parts record 174 further includes a communications link to several of automotive parts suppliers, and the parts record 174 includes competing prices for parts, availability of parts, the locations of the automotive suppliers, advertising materials, and discount coupons, if available.

Also, in the embodiment shown, the parts record 174 is in communication with an inventory record 176, which is a part supplier's updated and accurate record of the number of parts available in stock. Since the parts record 174 is in communication with the inventory record 176, the inventory figures can be reduced if the customer wishes to purchase a part, as will be described in greater detail below.

Furthermore, in the embodiment shown, the parts record 174 is in communication with an auction 178. The auction 178 is well known for facilitating competitive buying and selling. Several electronic auctions have been developed, and when linked to the parts record 174, the auction can be used via the console 160 to make competitive bids for needed automotive parts. Alternatively, if the customer is replacing automotive parts and wishes to sell the old parts, the auction can be used to make such a sale to the highest bidder.

As such, the process 100 continues in step 128, in which the defect report is correlated with the parts record 174. In other words, step 128 associates the particular defect with the appropriate parts that will be needed to correct that particular defect repair. It is also envisioned that the service report could be correlated with the parts record 174 in step 128. In either case, it is noted that the correlation of step 128 occurs directly or indirectly through the vehicle defect report. Also, with a more expansive embodiment of the parts record 174 described above, step 128 reveals where the needed parts can be obtained, how much they will cost, and if any discounts are available.

Next, in step 130 of the process 100, a parts report is generated. In one embodiment, the parts report is a saved compilation of the bulk of information revealed during step 128. In the embodiment in which the parts record 174 communicates with the auction 178, the parts report includes information about competitive bidding or selling in relation to the needed parts. As will be described in greater detail below, the parts report can save the customer money, and can inform the customer of a more convenient location for picking up the part.

Additionally, the process 100 continues in step 132, wherein the vehicle defect report, the service report, and the parts report are downloaded to the console 160. Preferably, the console 160 includes memory for electronically saving the downloaded information for later access. Moreover, in this embodiment, the console 160 assigns the saved information a unique identifier, such as a password, such that a user can access the previously downloaded information at a later time without having to repeat the full process 100.

Once downloaded, step 134 commences, wherein the console 160 prompts the customer for approval. In general, the console 160 gives options to the customer, such as whether to purchase a needed part or schedule a repair appointment. If an auction 178 is utilized, step 134 can involve approving the entry of a bid for a needed part (in the case of a purchase) or the step 134 can involve approving the acceptance of a competitive offer (in the case of a sale). In one embodiment, the console 160 also gives the customer the option of whether they would like an output of the defect report, service report, or parts report. At this point, the customer has the option of approving or disproving the output of the information.

If the customer approves of the transaction, step 136 commences, whereby money is tendered to the automotive care business. Money can be tendered before any of the information is outputted to the customer, and an individual price can be assigned for separately outputting the defect report, service report, and parts report. Costs might also include parts fees, scheduling fees, and the like. Also, payment for a part in step 136 causes the inventory figures to be reduced by the number of parts purchased.

Step 136 of the process can be completed by using credit card information obtained in step 102. As such, the customer simply approves that their credit card will be charged. In another embodiment, a payment mechanism 199, such as a magnetic data reader, an optical data reader, buttons used to input a credit card number, or cash machine, is included on the console 160 itself, and the user utilizes the payment mechanism 199 in a well known manner to complete step 136.

Finally, in step 138 of the process 100, the defect report, the service report, and the parts report is outputted by the console 160. As shown, an outputter 182 is connected to the console 160, the console 160 communicates output commands to the outputter 182, and the information is displayed to the customer for their review. In one embodiment, the outputter 182 comprises a widely-known printer, and the printer prints a hard copy for the customer.

Thus, the process 100 allows a vehicle owner to diagnose a vehicle and effectuate repairs on the same. The process 100 can reduce costs because the customer can choose the lowest priced parts and services from the list of available parts and services. Also, coupons and other advertising materials can be obtained through the process 100 to lower costs further. Additionally, the process allows the customer to diagnose the vehicle without having to pay the normally high costs of a professional diagnosis.

The process 100 also makes vehicle repair more convenient because the customer can choose when to diagnose the vehicle, as opposed to working around a professional's schedule to get a diagnosis. Furthermore, the customer can choose the closest and most convenient location to pick up parts or obtain repair services.

Moreover, an automotive care business can operate more efficiently by employing this process 100. For instance, if the business supplies parts, the console can be linked to its inventory system to automatically update those records. Also, the console can be linked to its scheduling records for automatically updating the same. Furthermore, parts can be sold electronically using the process 100, and thus workers can attend to other needs instead of spending time, completing these transactions. Finally, advertising materials transferred during the process 100 are likely to be effective because particular advertisements and coupons can be focused to customers with those particular automotive malfunctions.

Additional modifications and improvements of the present invention may also be apparent to those of ordinary skill in the art. Thus, the particular combination of parts described and illustrated herein is intended to represent only one embodiment of the present invention, and is not intended to serve as limitations of alternative devices within the spirit and scope of the invention. For example, FIG. 2 is a general illustration of one embodiment of the process 100 and database 162. FIG. 2 is not meant to limit the process 100 or database 162.

What is claimed is:

1. A customer driven process of diagnosing and repairing a vehicle comprising:
   a) temporarily providing a customer with an automotive diagnostic tool;
   b) receiving vehicle diagnostic signals from the diagnostic tool at a console;
   c) accessing a diagnostic database from the console;
   d) correlating the vehicle diagnostic signals to vehicle defect information in the diagnostic database;
   e) generating a vehicle defect report based on the correlation between the vehicle diagnostic signals and vehicle defect information;
   f) accessing a service database;
   g) correlating the vehicle defect report with service information in the service database, the service information including data relating to the cost to provide services to correct vehicle defect conditions;
   h) generating a service report based on the correlation between the vehicle defect report and the service information;
   i) accessing a parts database;
   j) correlating the vehicle defect report with parts information in the parts database, the parts information including data relating to the cost of vehicle parts needed to correct vehicle defect conditions at the automotive parts/service facility; and
   k) generating a parts report based on the correlation between the vehicle defect report and the parts information.

2. The process of claim 1, wherein the parts report includes information of a type chosen from a group consisting of needed parts, pricing of parts, availability of parts, location for obtaining parts, advertising materials, and discounts for purchasing parts.

3. The process of claim 1, wherein the service report includes information of a type chosen from a group consisting of needed repairs, availability of service, scheduling of services, pricing for services, service procedure details, time estimates for service, advertising materials, and discounts on service.

4. The process of claim 1, additionally comprising the step of providing instructions at the console as to how the customer needs to properly connect the diagnostic tool to the on-board computer.

5. The process of claim 1, wherein customer identification information is received in order to temporarily provide the diagnostic tool.

6. The process of claim 5, wherein the customer information includes customer credit card billing information.

7. The process of claim 1, further comprising storing the vehicle defect report, the service report, and the parts report and generating a customer identifier useful to access at least one of the vehicle defect report, the parts report, and the service report from the automotive parts/service facility.

8. The process of claim 5, wherein the customer information is utilized to bill payment for at least one of the vehicle defect report, the parts report, and the service report.

9. The process of claim 5 or 6, wherein the customer information is utilized to bill payment for a part needed to correct a vehicle defect.

10. The process of claim 5 or 6, wherein the customer information is utilized to bill payment for service needed to correct a vehicle defect.

11. The process of claim 5 or 6, wherein the customer information is utilized to schedule services needed to correct a vehicle defect.

12. The process of claim 6, wherein at least one of the vehicle defect report, the parts report, and the service report is outputted to the customer via the console.

13. The process of claim 6, wherein the parts database communicates with an inventory, and an inventory number is reduced after the part is paid for using the customer credit card billing information.

14. The process of claim 1, wherein at least one of the diagnostic database, the service database, and the parts database is associated with a web site that is remote to the console, accessible from the console via the Internet.

15. The process of claim 14, wherein the parts database communicates with an auction to competitively buy vehicle parts needed to correct vehicle defects.

16. The process of claim 1, wherein the console includes a payment mechanism.

17. The process of claim 16, wherein the payment mechanism is at least one of a magnetic data reader, an optical data reader, a plurality of buttons used to input a credit card number, and a cash machine.

18. The process of claim 1, wherein the diagnostic tool is provided to the customer upon payment of a rental fee.

19. The process of claim 1, wherein the service information further includes data relating to the ability of the automotive parts/service facility to provide services to correct the vehicle defect conditions.

20. The process of claim 1, wherein the parts information further includes data relating to the availability of vehicle parts needed to correct the vehicle defect conditions.

21. The process of claim 1, wherein step (b) includes wirelessly uploading the vehicle diagnostic signals from the diagnostic tool to a console at the automotive parts/service facility.

22. The process of claim 1, further comprising the steps of:
connecting a diagnostic tool to a vehicle on-board computer;
uploading vehicle diagnostic signals from the on-board computer to the diagnostic tool; and
returning the diagnostic tool to the automotive parts/service facility.

23. The process of claim 1, wherein the automotive diagnostic tool is temporarily provided at an automotive parts/service facility.

24. The process of claim 1, wherein steps (a)-(k) are implemented independent of the need for a customer to purchase or own any diagnostic equipment or computer equipment.

25. The process of claim 24, wherein steps (a)-(k) are implemented independent of the need for a customer to utilize any assistance or advice by a mechanic.

26. The process of claim 1, further comprising the step of scheduling services needed to correct a vehicle defect independent of input by an employee of an automotive parts/service facility.

* * * * *